(12) United States Patent
Kimoto

(10) Patent No.: US 12,430,015 B2
(45) Date of Patent: Sep. 30, 2025

(54) IMAGE DISPLAY APPARATUS INCLUDING DISPLAY CONTROLLER AND OPERATION ACCEPTANCE SECTION, IMAGE DISPLAY METHOD THEREFOR, AND PROGRAM THEREFOR

(71) Applicant: Konica Minolta, Inc., Tokyo (JP)

(72) Inventor: Takashi Kimoto, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 158 days.

(21) Appl. No.: 18/400,000

(22) Filed: Dec. 29, 2023

(65) Prior Publication Data
US 2024/0241628 A1    Jul. 18, 2024

(30) Foreign Application Priority Data
Jan. 17, 2023    (JP) .................................. 2023-005176

(51) Int. Cl.
*A61B 6/46* (2024.01)
*A61B 6/00* (2006.01)
*G06F 3/0481* (2022.01)
*G06F 3/04845* (2022.01)

(52) U.S. Cl.
CPC .......... *G06F 3/04845* (2013.01); *A61B 6/463* (2013.01); *A61B 6/54* (2013.01); *G06F 3/0481* (2013.01)

(58) Field of Classification Search
CPC .... G06F 3/0416; G06F 3/0412; G06F 3/0484; G06F 3/04886; G06F 3/04845; G06F 3/0481; A61B 8/463; A61B 8/465; A61B 6/463; A61B 6/465; A61B 6/54; A61B 8/467; A61B 8/469
See application file for complete search history.

(56) References Cited

U.S. PATENT DOCUMENTS

| | | | | |
|---|---|---|---|---|
| 9,330,497 | B2* | 5/2016 | Byrd | G06T 19/003 |
| 2002/0109735 | A1* | 8/2002 | Chang | A61B 6/463 |
| | | | | 715/853 |
| 2003/0095147 | A1* | 5/2003 | Daw | G01R 33/56 |
| | | | | 715/771 |
| 2011/0282206 | A1* | 11/2011 | Ichioka | G06F 3/0484 |
| | | | | 600/443 |
| 2014/0164997 | A1* | 6/2014 | Lee | G06F 3/04847 |
| | | | | 715/810 |

(Continued)

FOREIGN PATENT DOCUMENTS

JP    2011-255165 A    12/2011

*Primary Examiner* — Rinna Yi
(74) *Attorney, Agent, or Firm* — LUCAS & MERCANTI, LLP

(57) ABSTRACT

An image display apparatus according to an aspect of the invention includes: a display controller that performs display control on a display screen included in a display section; and an operation acceptance section, in which in a case where the operation acceptance section accepts a first operation of moving an operation position inward from a part of an edge portion of a display screen in a state where a first display element is displayed on the display screen, the display controller displays a second display element having a first display size on the display screen, and resizes the second display element to a second display size in a case where a predetermined condition is satisfied.

14 Claims, 11 Drawing Sheets

(56) References Cited

U.S. PATENT DOCUMENTS

| | | | |
|---|---|---|---|
| 2014/0276057 A1* | 9/2014 | Lee | A61B 8/463 |
| | | | 600/440 |
| 2015/0235373 A1* | 8/2015 | Kato | A61B 5/055 |
| | | | 348/51 |
| 2015/0363104 A1* | 12/2015 | Ichioka | A61B 8/465 |
| | | | 345/173 |
| 2021/0030399 A1* | 2/2021 | Tsubota | A61B 8/5207 |

* cited by examiner

IMAGE DISPLAY APPARATUS INCLUDING DISPLAY CONTROLLER AND OPERATION ACCEPTANCE SECTION, IMAGE DISPLAY METHOD THEREFOR, AND PROGRAM THEREFOR

CROSS REFERENCE TO RELATED APPLICATIONS

The entire disclosure of Japanese Patent Application No. 2023-005176 filed on Jan. 17, 2023, is incorporated herein by reference in its entirety.

BACKGROUND

Technological Field

The present disclosure relates to an image display apparatus, an image display method, and a program.

Description of the Related Art

As an example of an image display apparatus, an ultrasonic image diagnostic apparatus which transmits an ultrasonic wave to a subject, accepts and processes its echo signal, and generates an ultrasonic image has been widespread.

For example, Japanese Unexamined Patent Publication No. 2011-255165 discloses an image diagnostic apparatus which, when displaying an ultrasonic image and a menu relating to the ultrasonic image on a display section, accepts an input for designating a position on a display area of the display section and displays a menu associated in advance with the position designated by the input.

SUMMARY

In recent years, portable and small-sized ultrasonographic devices have been spreading. In a small-sized ultrasonographic device, the size of a display area included in a display section is often reduced. Therefore, it is difficult to display a plurality of display elements in the display area.

In the technology disclosed in Japanese Unexamined Patent Publication No. 2011-255165, a menu corresponding to a position specified by an input is displayed, and therefore, when the size of the display area becomes small, the ultrasonic image and the menu are displayed in an overlapping manner. Thus, a region of interest in an ultrasonic image that is necessary for performing a diagnosis is hidden by the menu and is less easily visible.

Furthermore, with the technology disclosed in Japanese Unexamined Patent Publication No. 2011-255165, a display position of a menu can be freely changed by an input operation for changing a position associated with each menu. However, since the display position itself of each menu displayed in the display area is not changed, an input operation for changing the display position of each menu is complicated.

An object of the present disclosure is to provide an image display apparatus, an image display method, and a program capable of displaying each display element in a display area at an appropriate position by a simple operation.

To achieve at least one of the abovementioned objects, according to an aspect of the present invention, an image display apparatus according to an aspect of the present disclosure include: a display controller that performs display control on a display screen included in a display section; and an operation acceptance section, in which in a case where the operation acceptance section accepts a first operation of moving an operation position inward from a part of an edge portion of a display screen in a state where a first display element is displayed on the display screen, the display controller displays a second display element having a first display size on the display screen, and resizes the second display element to a second display size in a case where a predetermined condition is satisfied.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Configuration of Ultrasonographic Device 1

Figure 1:
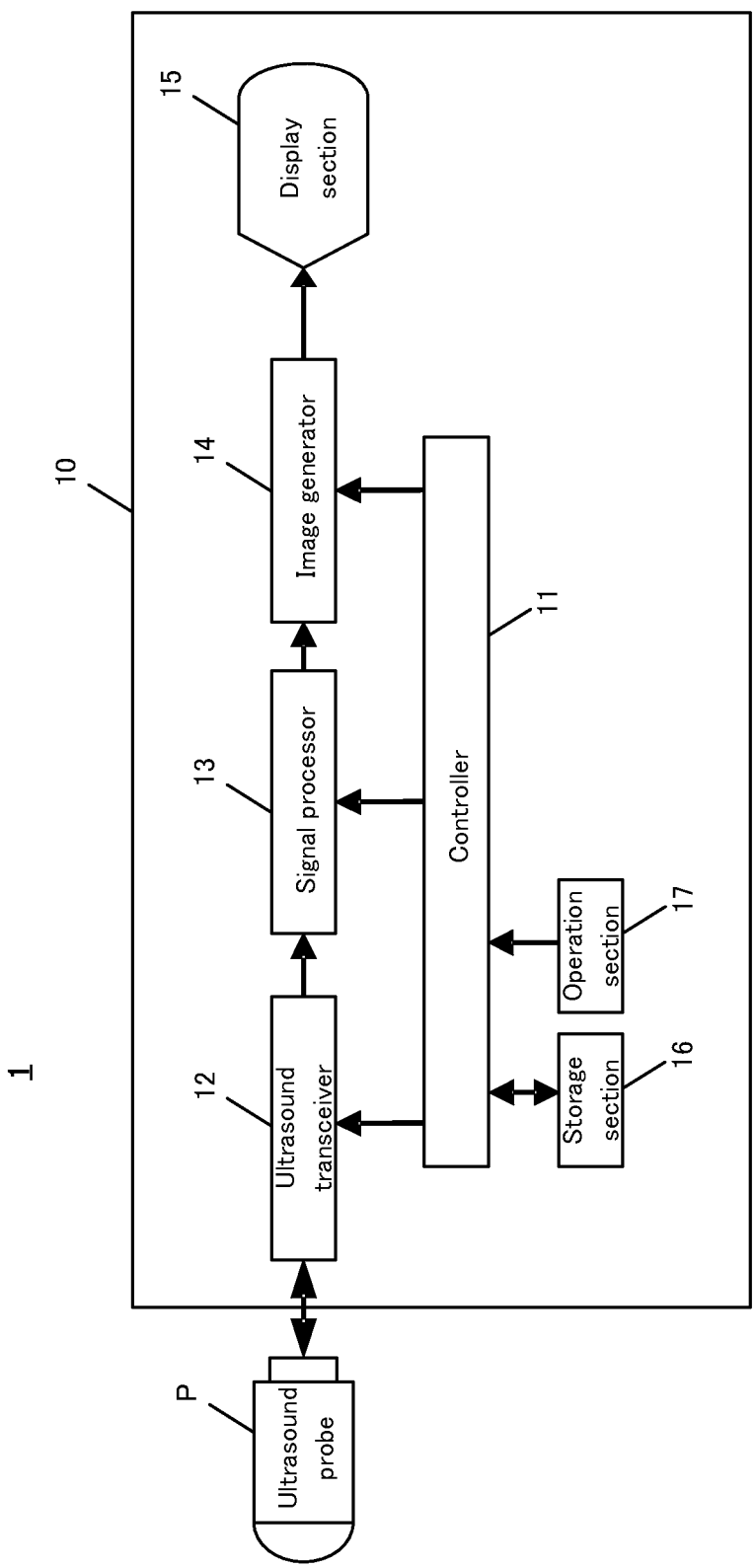
FIG. 1 is a block diagram illustrating a configuration of an ultrasonographic device according to an embodiment of the present disclosure.

FIG. 1 is a block diagram illustrating a configuration of an ultrasonographic device 1 according to an embodiment of the present disclosure. The ultrasonographic device 1 is one example of the image display apparatus according to the embodiment of the present disclosure.

As illustrated in FIG. 1, the ultrasonographic device 1 includes an ultrasonographic device body 10 and an ultrasound probe P.

The ultrasound probe P transmits an ultrasonic wave to a subject such as a living body (not illustrated) and accepts a reflection wave (reflection echo) of the ultrasonic wave reflected on the subject. The ultrasound probe P acquires a reception signal, which is an electrical signal, from the received reflected echo, and outputs the reception signal to the ultrasonographic device body 10.

The ultrasonographic device body 10 is connected to the ultrasound probe P via a cable or the like. The ultrasonographic device body 10 transmits a transmission signal of an electric signal to the ultrasound probe P to cause the ultrasound probe P to transmit ultrasonic waves to the subject. Further, the ultrasonographic device body 10 images and displays the internal state of the subject as an ultrasonic image based on the reception signal received from the ultrasound probe P.

As illustrated in FIG. 1, the ultrasonographic device body 10 includes a controller 11, an ultrasound transceiver 12, a signal processor 13, an image generator 14, a display section 15, a storage section 16, and an operation section 17.

The controller 11 performs overall control of the ultrasonographic device 1. The controller 11 is, for example, a processor having a central processing unit (CPU), a random access memory (RAM), and the like. The controller 11 integrally controls the operation of the ultrasonographic device 1 by executing various processes in cooperation with various programs stored in the storage section 16.

The ultrasound transceiver 12 supplies a transmission signal to the ultrasound probe P, and causes the ultrasound probe P to generate ultrasound. Further, the ultrasound transceiver 12 receives a reflected echo generated in the subject by the ultrasound probe P, generates a reception signal, and outputs the reception signal to the signal processor 13.

The signal processor 13 electrically amplifies a reception electric signal obtained by converting the reception signal, performs signal processing such as digital conversion, and outputs the signal to the image generator 14.

The image generator 14 generates an ultrasonic image (for example, a B-mode image) based on the digital reception signal output by the ultrasound transceiver 12. The B-mode image represents the intensity of a reception signal by luminance. The ultrasonic image generated by the image generator 14 is stored in a frame memory or the like (not illustrated) in units of frame images. When the ultrasonic image is output from the image generator 14, the controller 11 overwrites the frame memory or the like with the output ultrasonic image in units of frames and causes the display section 15 to display the image.

The display section 15 is a display device such as a liquid crystal display (LCD), a cathode-ray tube (CRT) display, an organic electronic luminescence (EL) display, or a plasma display. Under the control of a display controller 111 (see FIG. 2) described later, the display section 15 displays various screens in the display area. Details of the various screens will be described later.

The storage section 16 is constituted by, for example, a hard disk drive (HDD) or a semiconductor nonvolatile memory. The storage section 16 stores various programs and data necessary for execution of the programs.

Further, the storage section 16 may store information on a subject (patient) to be diagnosed based on an ultrasonic image generated by the ultrasonographic device 1. Furthermore, the storage section 16 may store information on various display objects (details will be described later) such as a body mark, a measurement result, and an annotation to be displayed on the display section 15.

The operation section 17 is an operation device such as various switches, function buttons, a trackball, a mouse, and a keyboard. In this exemplary embodiment, the operation section 17 includes, in particular, a touch pad disposed so as to overlap a display device constituting the display section 15. That is, the display section 15 and the operation section 17 form a so-called touch panel. Thus, the operation section 17 can receive a user's intuitive operation corresponding to the display content of the screen displayed on the display section 15. The operation section 17 outputs a generated operation signal to the controller 11 based on an operation by a user of the ultrasonographic device 1.

Figure 2:
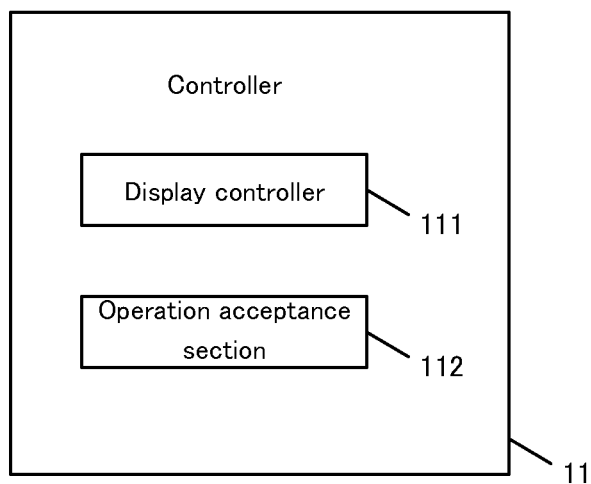
FIG. 2 is a diagram illustrating functional blocks included in the controller.

FIG. 2 is a diagram illustrating functional blocks included in the controller 11. As illustrated in FIG. 2, the controller 11 includes a display controller 111 and an operation acceptance section 112.

The display controller 111 generates a screen to be displayed on the display section 15 based on the ultrasonic image or the like generated by the image generator 14. Examples of the screen that the display controller 111 causes the display section 15 to display include a diagnostic screen on which an ultrasonic image continues to be updated so that the latest ultrasonic image is always displayed and a still image screen on which an ultrasonic image at a certain time point continues to be displayed and on which the size or the like of a structure included in the ultrasonic image can be measured.

When an examination on a certain subject (a patient or the like) is performed using the ultrasonographic device 1, a user such as a doctor appropriately performs diagnosis while viewing a diagnosis screen on which a real-time ultrasonic image based on an ultrasonic signal obtained from the subject is displayed. When the user wants to measure the size of a structure (an organ, a fetus, or the like) in the subject during diagnosis, the user can measure the size of the structure by stopping the display screen of the display section 15 and designating two points on the ultrasonic image.

The operation acceptance section 112 accepts a user operation via the operation section 17.

Display Aspect

Hereinafter, a display mode of the display section 15 in the ultrasonographic device 1 having the above-described configuration will be described.

Figure 3:
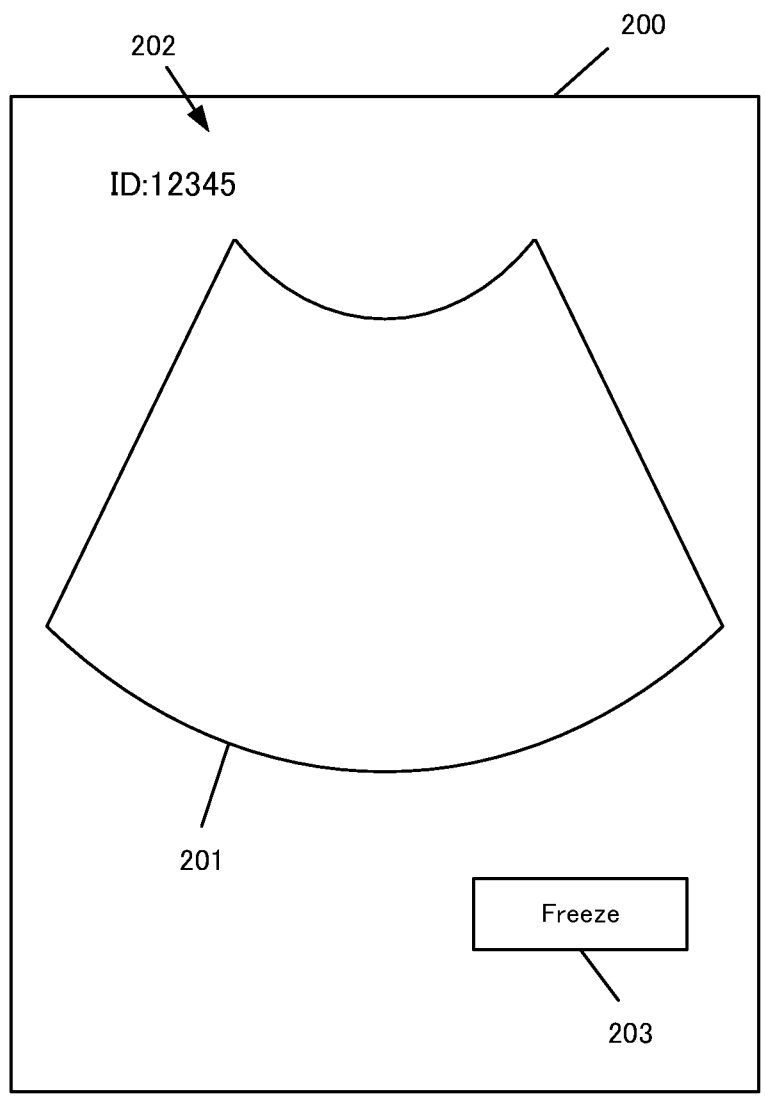
FIG. 3 is a diagram illustrating an example of a basic screen displayed on the display section of the ultrasonographic device.

FIG. 3 is a view illustrating a basic screen 200 displayed on the display section 15 of the ultrasonographic device 1. As illustrated in FIG. 3, the basic screen 200 includes, as display elements, an ultrasonic image display field 201, an identification information display field 202, and a switching button 203. The basic screen 200 is the most basic screen among a plurality of types of display screens displayed on the display section 15. For example, when performing a medical examination on the subject, the user performs the medical examination in a state where the basic screen 200 is displayed on the display section 15.

The ultrasonic image display field 201 is an example of a first display element of the present disclosure.

The ultrasonic image display field 201 is a field for displaying an ultrasonic image generated by the image generator 14 based on reflected waves from the subject with respect to transmission waves transmitted from the ultrasound probe P. The ultrasonic image displayed in the ultrasonic image display field 201 is a moving image updated at a predetermined cycle or a still image in which an image at a certain timing is continuously displayed. The ultrasonic image displayed in the ultrasonic image display field 201 is switched between a moving image and a still image based on the operation of the switching button 203 by the user.

In a case where the ultrasonic image displayed in the ultrasonic image display field 201 is a moving image, a change in the position of the ultrasound probe P or a movement (a heartbeat, a fetal movement, or the like) of a structure inside the subject is reflected in the ultrasonic image as needed, and the user can thus perform diagnosis based on the latest image. On the other hand, in a case where the ultrasonic image displayed in the ultrasonic image display field 201 is a still image, a structure appearing in the image is stationary, and the user can examine a specific structure or the like in detail.

The identification information display field 202 is a field in which information capable of identifying the subject corresponding to the ultrasonic image displayed in the ultrasonic image display field 201 is displayed. In the example illustrated in FIG. 3, the identification number of the subject is displayed in the identification information display field 202, but the information displayed in the identification information display field 202 may be other information, for example, a patient name.

The switching button 203 is an operation button for receiving an operation of switching the ultrasonic image displayed in the ultrasonic image display field 201 between a moving image and a still image. For example, each time the user operates the switching button 203 through the operation section 17, the ultrasonic image displayed in the ultrasonic image display field 201 is switched from a moving image to a still image or from a still image to a moving image.

In the example illustrated in FIG. 3, the display section 15 has a vertically long screen, and on the basic screen 200, an identification information display field 202 is displayed at the uppermost part of the screen, an ultrasonic image display field 201 is disposed below the identification information display field 202, and a switching button 203 is disposed below the ultrasonic image display field 201. Note that the display position of each display element illustrated in FIG. 3 is an example, and each display element may be displayed at another position.

In the basic screen 200, the display size of the ultrasonic image display field 201 is set to an appropriate size. The appropriate size is, for example, a size designated by the user so that the display content of the ultrasonic image display field 201 is easily visually recognized, or a size set by the display controller 111 in accordance with the size of the entire screen of the display section 15.

In the basic screen 200 illustrated in FIG. 3, supplementary information related to the ultrasonic image displayed in the ultrasonic image display field 201 is not displayed. Accordingly, even in a case in which the display section 15 has a relatively small size, the display size of the ultrasonic image display field 201 can be increased as much as possible. The supplementary information will be described later.

Figure 5:
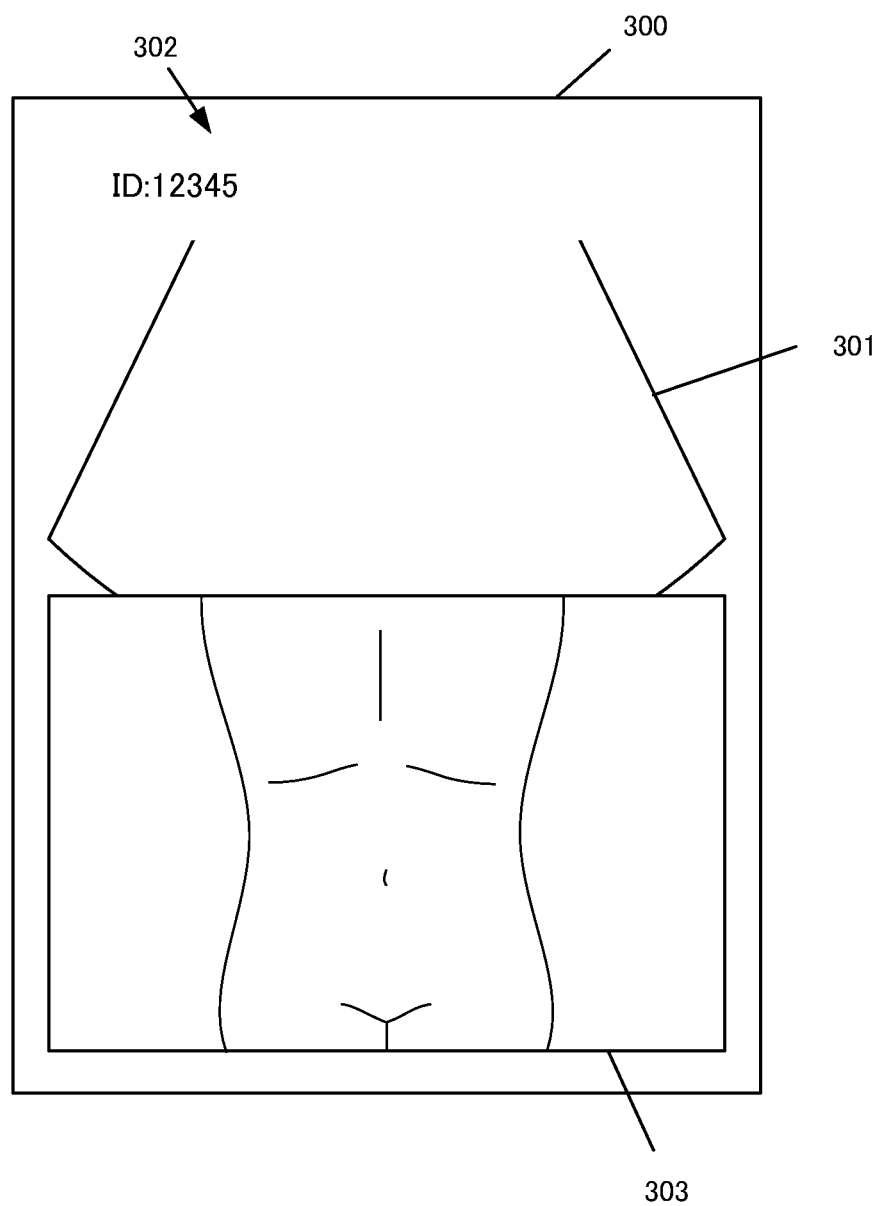
FIG. 5 is a diagram illustrating an example of the first supplementary information display screen.

When the operation acceptance section 112 accepts an operation for moving the operation position from a part of an edge portion of the screen of the display section 15 toward the inside of the screen in a state where the basic screen 200 is displayed on the display section 15, the display controller 111 allows a first supplementary information display screen 300 illustrated in FIG. 5 to be displayed. Note that the operation position is a position specified by a user's operation, and specifically, a position at which a user's finger contacts a touch panel composed of the display section 15 and the operation section 17. Hereinafter, an operation for moving the operation position from part of an edge portion of the screen of the display section 15 toward the inside of the screen will be described as a first operation.

Figure 4:
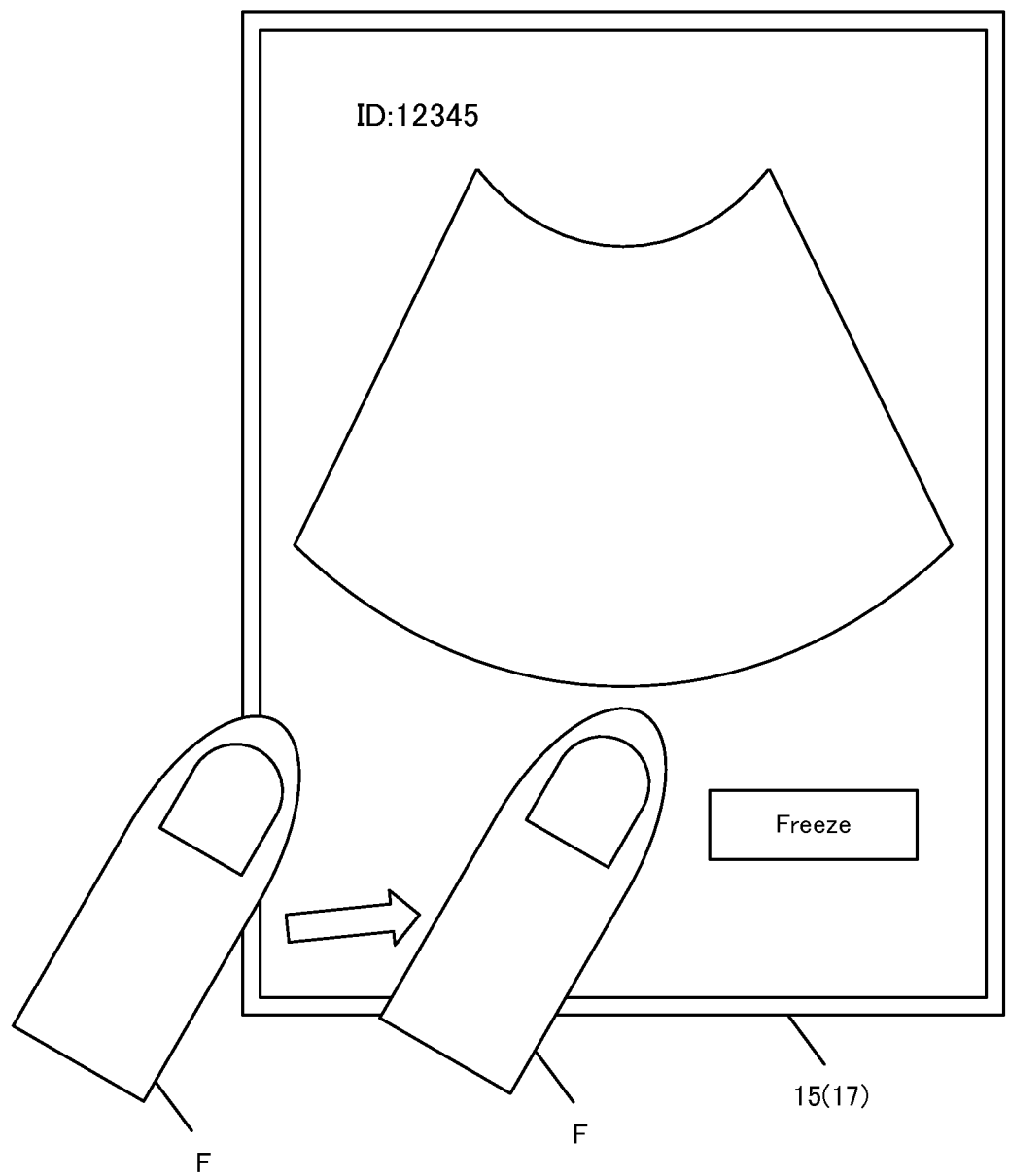
FIG. 4 is a diagram schematically illustrating the first operation for switching from the basic screen to the first supplementary information display screen.

FIG. 4 is a diagram schematically illustrating the first operation. FIG. 5 is a diagram illustrating the first supplementary information display screen 300.

FIG. 4 illustrates a state in which a user moves a finger F from part of an edge portion of the screen of the display section 15 toward the inside of the screen while keeping the finger F in contact with the touch panel that is the operation section 17 and then releases the finger F. Such an operation of moving the finger from one place to another place and then releasing the finger from the touch panel is generally referred to as a drag operation. That is, the first operation illustrated in FIG. 4 is a drag operation from a part of the edge portion toward the inside of the screen.

Note that in the example illustrated in FIG. 4, the first operation is a drag operation in which a user moves a finger F with respect to the touch panel serving as the operation section 17 from part of an edge portion of the screen toward the inside of the screen, but the present disclosure is not limited thereto. For example, the user may perform the first operation using another operation tool, such as a touch pen, instead of a finger. Furthermore, even in a case where the operation section 17 is a mouse, a drag operation is possible, and a user may perform the first operation using the mouse. Further, for example, the same applies to a case where the operation section 17 includes a trackball for moving the operation position and a button for designating the operation position. Specifically, first operation may also be accepted when the user presses the button to designate the operation position on a part of the edge portion of the screen and then moves the operation position using the trackball in a state where the button is pressed.

In the example illustrated in FIG. 4, the part of the edge portion which is the start position of the first operation is the left end of the screen of the display section 15, but the present disclosure is not limited thereto. The start position of the first operation may be any position of the edge portion. In addition, in the first operation, the inside of the screen is, for example, a position separated from all edge portions of the screen of the display section 15 by a distance equal to or greater than a predetermined distance.

Upon receiving the first operation illustrated in FIG. 4, the ultrasonographic device 1 switches the screen displayed on the display section 15 from the basic screen 200 to the first supplementary information display screen 300 illustrated in FIG. 5. The first supplementary information display screen 300 illustrated in FIG. 5 includes an ultrasonic image display field 301, an identification information display field 302, and a supplementary information display field 303.

The ultrasonic image display field 301 is an example of a first display element of the present disclosure. The supplementary information display field 303 is an example of a second display element of the present disclosure.

The supplementary information display field 303 is a field for displaying supplementary information on the ultrasonic image displayed in the ultrasonic image display field 301. The supplementary information includes information related to the ultrasonic image, information related to the subject of the ultrasonic image, or the like. Specific examples of the supplementary information include a body mark, an annotation, measurement information, patient information, and an image parameter. The body mark is a mark indicating which position of the subject the ultrasound probe P that transmits ultrasound waves is making contact with. The annotation is a character string indicating the content or the like of the ultrasonic image displayed in the ultrasonic image display field 201. The measurement information is information indicating an actual distance between two points designated by the user in the ultrasonic image displayed in the ultrasonic image display field 201. The patient information is information excluding the information displayed in the identification information display field 302 from the information on the subject (patient). The image parameter is information including parameters of the ultrasonic image to be displayed in the ultrasonic image display field 201, that is, various parameters such as luminance, brightness, and contrast.

On the first supplementary information display screen 300 illustrated in FIG. 5, a body mark is displayed in the supplementary information display field 303. In the example illustrated in FIG. 5, only the body mark is displayed in the supplementary information display field 303, but in the present disclosure, one or more types of supplementary information other than the body mark may be displayed in the supplementary information display field 303.

On the first supplementary information display screen 300 illustrated in FIG. 5, an ultrasonic image display field 301 and a supplementary information display field 303 are displayed vertically side by side. In the following description, the display size of the supplementary information display field 303 in the first supplementary information display screen 300 is referred to as a first display size. In the example illustrated in FIG. 5, the first display size is a size equal to or larger than the display size of the ultrasonic image display field 301. Accordingly, the user can easily visually recognize the display content of the supplementary information display field 303.

Since the display size of the supplementary information display field 303 is set to a size equal to or larger than that of the ultrasonic image display field 301, in the example illustrated in FIG. 5, a part of the ultrasonic image display field 301 is covered with the supplementary information display field 303. Furthermore, although not illustrated in FIG. 5, a switching button equivalent to the switching button 203 on the basic screen 200 illustrated in FIG. 4 may also be in a state of being covered with the supplementary information display field 303.

The supplementary information displayed in the supplementary information display field 303 is, for example, supplementary information specified in advance by the user. Alternatively, for example, the type of supplementary information displayed in the supplementary information display field 303 may be changed according to the start position of the first operation.

In specific examples, in a case where the display section 15 has a rectangular display screen, a body mark may be displayed in the supplementary information display field 303 when the left side of the four edge portions is the start position, an annotation may be displayed in the supplementary information display field 303 when the right side is the start position, measurement information may be displayed in the supplementary information display field 303 when the upper side is the start position, and patient information may be displayed in the supplementary information display field 303 when the lower side is the start position. In addition, for example, in a case where the start position is the left or right edge portion, supplementary information different between the upper half and the lower half may be displayed in the supplementary information display field 303. In a case where the start position is the upper or lower edge portion, supplementary information different between the left half and the right half may be displayed in the supplementary information display field 303.

Alternatively, for example, the type of supplementary information displayed in the supplementary information display field 303 may be changed based on whether the ultrasonic image displayed in the ultrasonic image display field 301 is a moving image or a still image. In a specific example, when the first operation is accepted in a state where the ultrasonic image displayed in the ultrasonic image display field 301 is a moving image, a body mark may be displayed in the supplementary information display field 303, and when the first operation is accepted in a state where the ultrasonic image is a still image, an annotation may be displayed in the supplementary information display field 303.

In the first supplementary information display screen 300, when the supplementary information display field 303 is displayed so as to overlap a part of the ultrasonic image display field 301, display may be such that the region of interest of the ultrasonic image displayed in the ultrasonic image display field 301 does not overlap the supplementary information display field 303. The region of interest in the ultrasonic image may be designated by the user via the operation section 17, or may be derived based on a known image analysis technique, for example.

As described above, since the supplementary information display field 303 is displayed in the first display size which is relatively large on the first supplementary information display screen 300, the user can easily visually recognize the display content of the supplementary information display field 303. However, by displaying the supplementary information display field 303 in the first display size, the space for displaying the entire ultrasonic image display field 301 in the display screen of the display section 15 becomes insufficient, and the supplementary information display field 303 is displayed to overlap a part of the ultrasonic image display field 301. In this state, it is difficult for the user to visually recognize the entire ultrasonic image displayed in the ultrasonic image display field 301.

Figure 6:
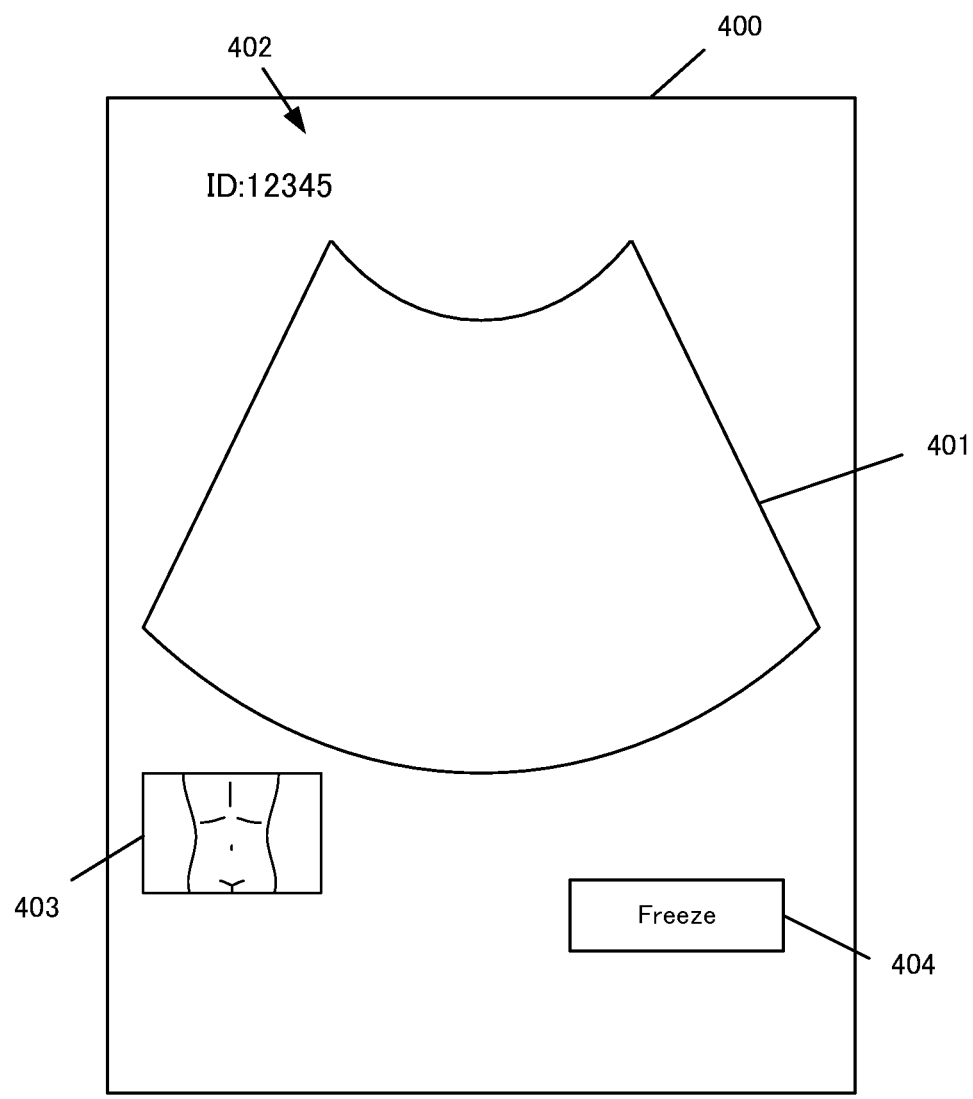
FIG. 6 is a diagram illustrating an example of the second supplementary information display screen.

In order to improve this state, when a predetermined condition is satisfied in a state in which the first supplementary information display screen 300 is displayed on the display section 15, the display controller 111 causes the display content of the display section 15 to transition to a second supplementary information display screen 400 exemplified in FIG. 6.

FIG. 6 is an illustration of a second supplementary information display screen 400. As illustrated in FIG. 6, the second supplementary information display screen 400 includes an ultrasonic image display field 301, an identification information display field 402, a supplementary information display field 403, and a switching button 404.

The ultrasonic image display field 401 is an example of a first display element of the present disclosure. The supplementary information display field 403 is an example of a second display element of the present disclosure.

As illustrated in FIG. 6, on the second supplementary information display screen 400, the display size of the supplementary information display field 403 is smaller than the supplementary information display field 303 illustrated in FIG. 5. In the following description, the display size of the supplementary information display field 403 in the second supplementary information display screen 400 is referred to as a second display size. The second display size is a size smaller than the first display size.

The second display size is, for example, a size allowing the user to visually recognize the display content of the supplementary information display field 403 and allowing the supplementary information display field 403 to be displayed without overlap with the ultrasonic image display field 401. In this way, on the second supplementary information display screen 400, the supplementary information display field 403 is displayed in the second display size such that the supplementary information display field does not overlap the ultrasonic image display field 401. Thus, the ultrasonic image displayed in the ultrasonic image display field 401 is more easily visually recognized on the second supplementary information display screen 400 than on the first supplementary information display screen 300. Therefore, even in a case in which the size of the display area of the display section 15 is relatively small, the user can check the supplementary information and perform diagnosis using the ultrasonic image at the same time on the second supplementary information display screen 400. In addition, since the switching button 404 for switching the ultrasonic image between the moving and static images is not covered with the supplementary information display field 403 and can be visually recognized, the user can perform a switching operation of switching between the moving and static images.

As the predetermined condition for transition from the first supplementary information display screen 300 to the second supplementary information display screen 400, for example, the following condition can be set.

The first condition is that a predetermined time elapses after the transition from the basic screen 200 to the first supplementary information display screen 300. In a case where the first condition is adopted, the display controller 111 determines that the first condition is satisfied when a predetermined time elapses after the transition from the basic screen 200 to the first supplementary information display screen 300 by the first operation of the user, in other words, after the time point when the display of the first supplementary information display screen 300 is started. The predetermined time is, for example, 10 seconds.

The second condition is that the user performs a second operation for confirming the state in which the supplementary information is displayed on the screen. The second operation is, for example, an operation of dragging and moving the supplementary information display field 303 to a part of the edge portion of the screen on the first supplementary information display screen 300.

Figure 7:
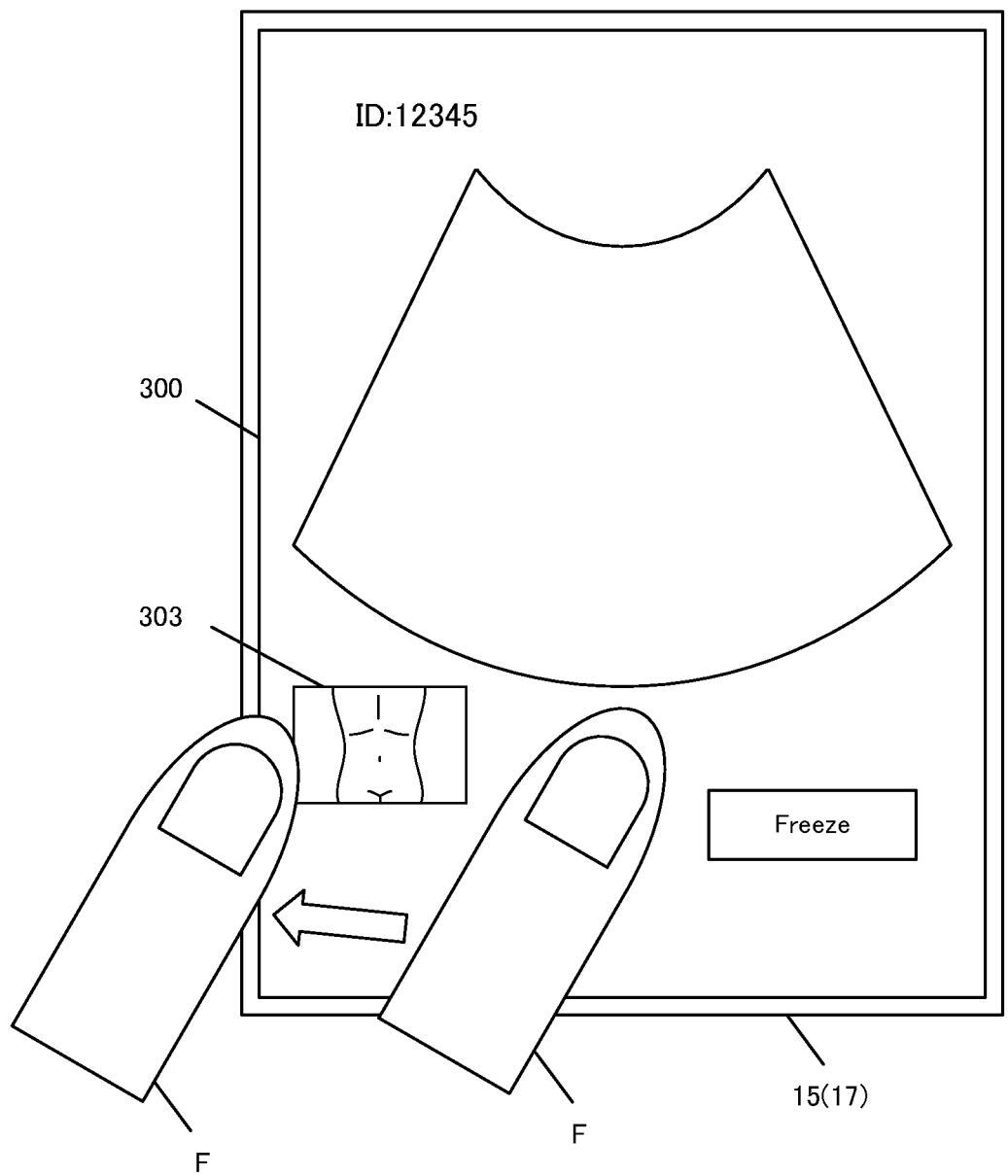
FIG. 7 is a diagram schematically illustrating the second operation for switching from the first supplementary information display screen to the second supplementary information display screen.

FIG. 7 is a diagram schematically illustrating a second operation for switching from the first supplementary information display screen 300 to the second supplementary information display screen 400. As illustrated in FIG. 7, in the second operation, the finger of the user drags and moves the supplementary information display field 303 on the first supplementary information display screen 300. The second operation is an operation in which the movement destination of the operation position by the drag operation is the edge portion of the screen. In other words, the second operation is an operation of dragging and moving the supplementary information display field 303 displayed on the screen of the display section 15 to the outside of the screen. When such a second condition is adopted, the display controller 111 determines that the second condition is satisfied when the operation acceptance section 112 accepts the second operation.

As described above, in the ultrasonographic device 1 of the present disclosure, after the screen display of the display section 15 is transitioned from the basic screen 200 to the first supplementary information display screen 300 based on the first operation, the screen display is further transitioned to the second supplementary information display screen 400 when a predetermined condition is satisfied. Accordingly, when the user wants to check the supplementary information on the basic screen 200 on which the supplementary information is not displayed, the supplementary information can be displayed in a relatively large display size by a simple operation (first operation). Thus, the user can easily visually recognize the supplementary information even though the size of the display area of the display section 15 is relatively small. Further, when a predetermined condition is satisfied in the first supplementary information display screen 300, the screen transitions to the second supplementary information display screen 400 in which the supplementary information display field 403 is reduced and displayed so as not to overlap the ultrasonic image display field 401 and the switching button 404. Therefore, even when the size of the display area of the display section 15 is relatively small, the user can perform diagnosis using the ultrasonic image while checking the supplementary information.

MODIFICATION EXAMPLES OF DISPLAY ASPECT

In the above description, the supplementary information display field 303 is displayed in the relatively large first display size on the first supplementary information display screen 300, and the ultrasonic image display field 301 and the supplementary information display field 303 are displayed side by side in a state where a part of the ultrasonic image display field 301 is covered with the supplementary information display field 303. Such a display aspect is merely an example of the present disclosure, and other display aspects can be applied for the first supplementary information display screen in the present disclosure. Hereinafter, a modification example of the display aspect of the first supplementary information display screen of the present disclosure will be described.

First Modification

Figure 8:
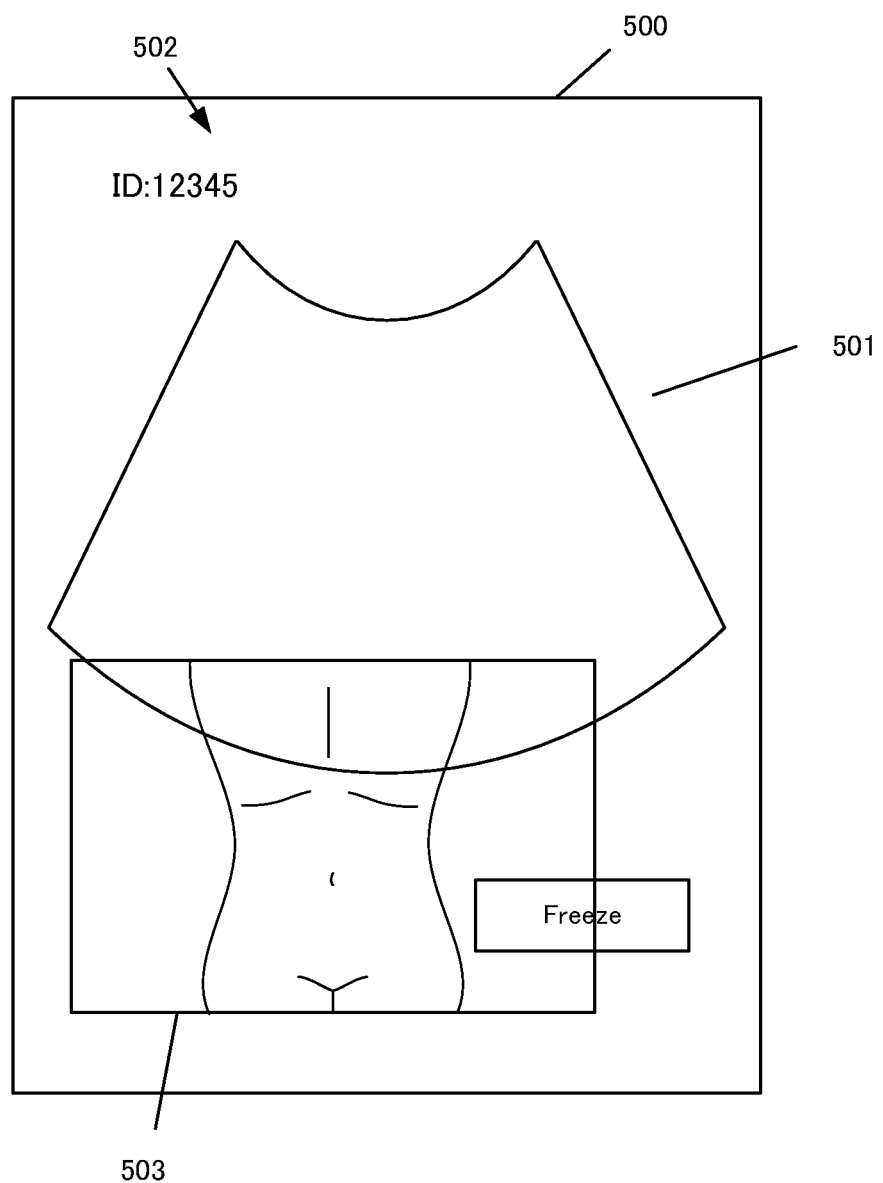
FIG. 8 is a diagram for explaining a first modification example of the first supplementary information display screen.

FIG. 8 is a diagram for explaining a first modification of the first supplementary information display screen. The first supplementary information display screen 500 illustrated in FIG. 8 includes an ultrasonic image display field 501, an identification information display field 502, and a supplementary information display field 503. In the first modification example illustrated in FIG. 8, a body mark is displayed in the supplementary information display field 503 similarly to the supplementary information display field 303 of the first supplementary information display screen 300 illustrated in FIG. 5, but the present disclosure is not limited thereto, and other types of supplementary information may be displayed.

In the first modification example illustrated in FIG. 8, the supplementary information display field 503 is displayed in a transparent manner. Therefore, although the ultrasonic image display field 501 and the supplementary information display field 503 are displayed so as to partially overlap each other, the user can view both the ultrasonic image displayed in the ultrasonic image display field 501 and the supplementary information displayed in the supplementary information display field 503.

Similarly to the above description, the first supplementary information display screen 500 illustrated in FIG. 8 transitions to the second supplementary information display screen 400 illustrated in FIG. 6 when a predetermined condition is satisfied. Accordingly, the user can visually recognize the entire ultrasonic image of the ultrasonic image display field 501 displayed so as to overlap the supplementary information display field 503 on the second supplementary information display screen 400.

Second Modification

Figure 9:
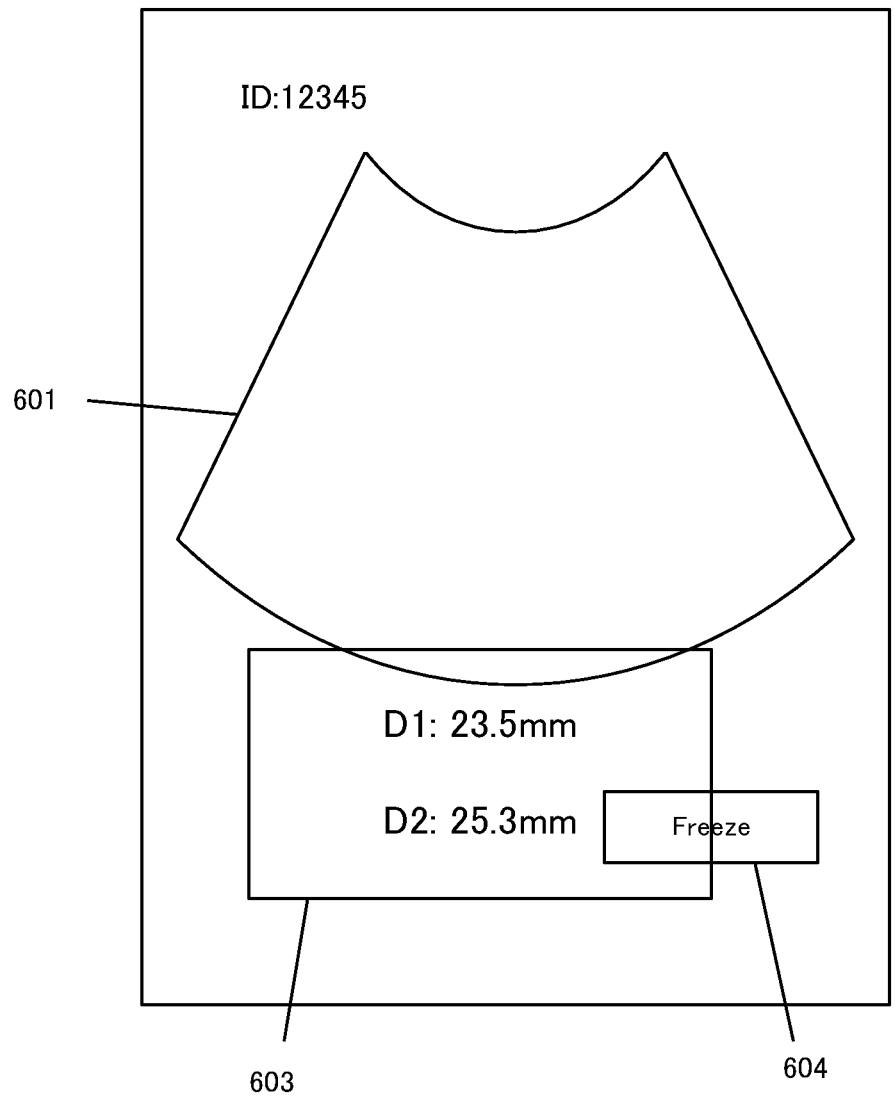
FIG. 9 is a diagram for explaining a second modification example of the first supplementary information display screen.

FIG. 9 is a diagram for explaining a second modification of the first supplementary information display screen. In the first supplementary information display screen 300 illustrated in FIG. 5, a body mark is displayed as an example of supplementary information in the supplementary information display field 303, but in FIG. 9, a first supplementary information display screen 600 in which measurement information is displayed in the supplementary information display field 603 is illustrated. In the example illustrated in FIG. 9, the supplementary information display field 603 is displayed so as to overlap the ultrasonic image display field 601 and the switching button 604. In this case, in a second supplementary information display screen (not illustrated) to which a transition is made when a predetermined condition is satisfied in a state where the first supplementary information display screen 600 is displayed, measurement information is also displayed in the supplementary information display field. As described above, the ultrasonographic device 1 of the present disclosure can display various types of supplementary information in the display field of each screen in an appropriate display size.

Third Modification

Figure 10:
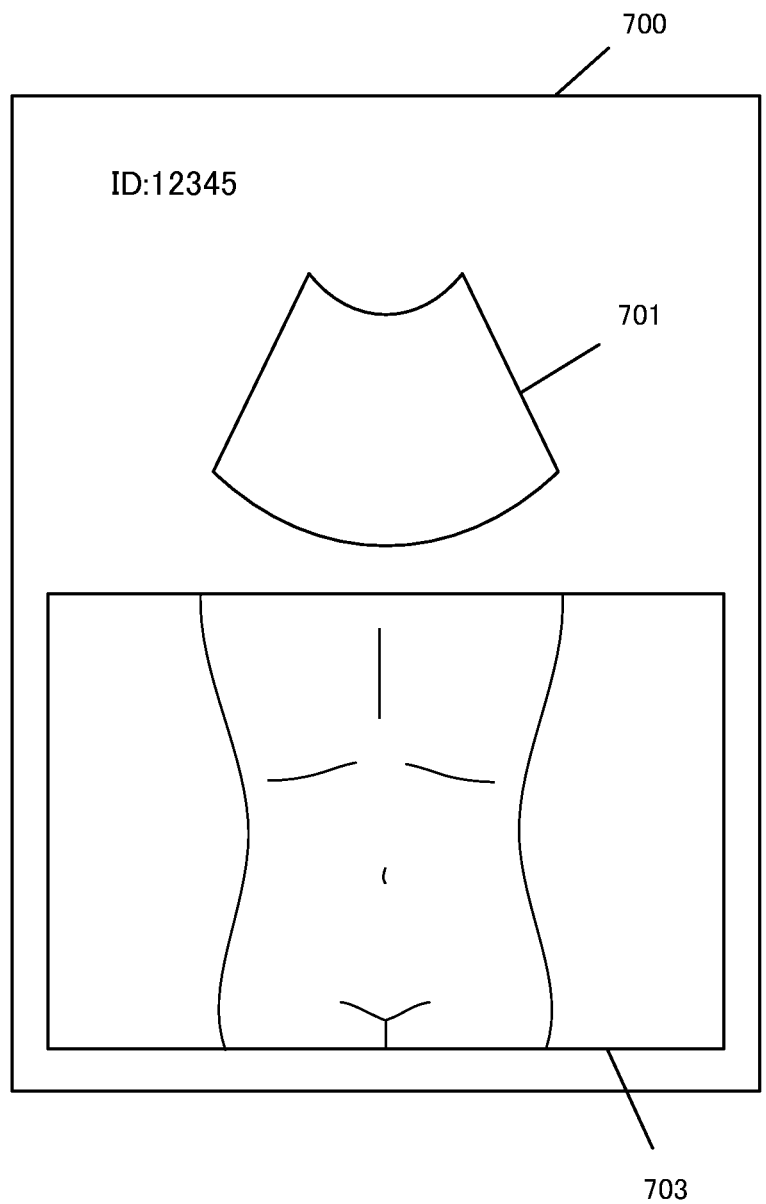
FIG. 10 is a diagram for explaining a third modification example of the first supplementary information display screen.

FIG. 10 is a diagram for explaining a third modification of the first supplementary information display screen. On the first supplementary information display screen 700 of the third modification example, the ultrasonic image display field 701 is reduced and displayed so as not to overlap the supplementary information display field 703 of the first display size. Therefore, the user can visually recognize the entire ultrasonic image on the first supplementary information display screen 700.

Also in the first supplementary information display screen 700 illustrated in FIG. 10, similarly to the above description, transition to the second supplementary information display screen 400 illustrated in FIG. 6 is made in a case where a predetermined condition is satisfied. Accordingly, since the display size of the ultrasonic image display field 701 returns to the same size as the display size on the basic screen 200, the user can perform diagnosis using the ultrasonic image while checking the supplementary information.

EXEMPLARY OPERATION

Figure 11:
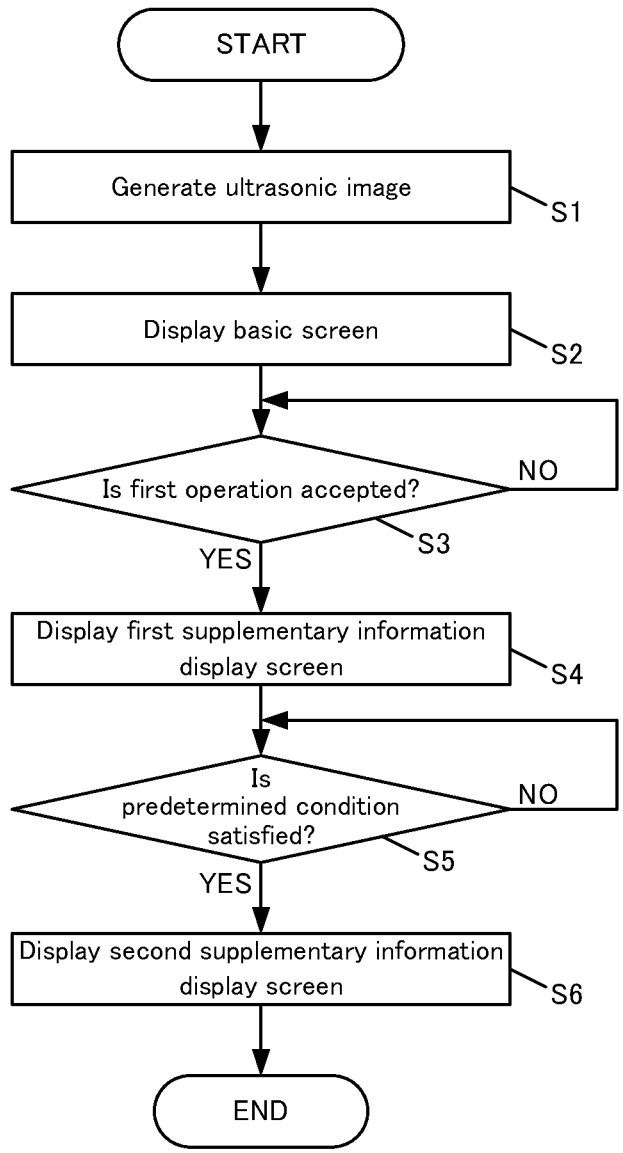
FIG. 11 is a diagram for explaining an operation example of the ultrasonographic device.

An example of operation of the ultrasonographic device 1 will be described below. FIG. 11 is a diagram for explaining an operation example of the ultrasonographic device 1.

In step S1, the controller 11 of the ultrasonographic device 1 generates an ultrasonic image based on a user's operation or the like. The user's operation in step S1 is, for example, an image generation start operation via the operation section 17 or to press a button for starting ultrasonic image generation that is disposed on the ultrasound probe P.

In step S2, the controller 11 causes the display section 15 to display the basic screen 200 illustrated in FIG. 3 using the ultrasonic image generated in step S1.

In step S3, the controller 11 determines whether or not the first operation is performed on the operation section 17. As described above, the first operation is an operation of moving the operation position from a part of the edge portion of the screen to the inside of the screen in a state where the basic screen 200 is displayed.

When it is determined in step S3 that the first operation has been performed (step S3: YES), the controller 11 allows the operation to proceed to step S4, or otherwise (step S3: NO), the operation of step S3 is repeated.

In step S4, the controller 11 causes the display section 15 to display the first supplementary information display screen 300 illustrated in FIG. 5.

In step S5, the controller 11 determines whether or not a predetermined condition is satisfied. As described above, the predetermined condition is either that a predetermined time elapses after the first supplementary information display screen 300 is displayed or that the second operation is performed on the operation section 17. As described above, the second operation is an operation of dragging and moving the supplementary information display field 303 on the first supplementary information display screen 300 to a part of the edge portion of the screen.

When it is determined in step S5 that the predetermined condition is satisfied (step S5: YES), the controller 11 allows the operation to proceed to step S6, or otherwise (step S5: NO), the operation of step S5 is repeated.

In step S6, the controller 11 causes the display section 15 to display the second supplementary information display screen 400 illustrated in FIG. 6.

According to the above operation example, the ultrasonographic device 1 can cause the display to transition to the first supplementary information display screen 300 including the supplementary information display field 303 in which the supplementary information is displayed in the relatively large first display size by the simple and intuitive first operation on the basic screen 200 in which the supplementary information is not displayed. Thus, even when the size of the display area of the display section 15 is relatively small, the user can quickly check the supplementary information on the ultrasonic image displayed on the basic screen 200.

In the first supplementary information display screen 300, a part of the ultrasonic image display field 301 is covered with the supplementary information display field 303. However, when a predetermined condition is satisfied in a state where the first supplementary information display screen 300 is displayed, the display can be transitioned to the second supplementary information display screen 400 in which the entire ultrasonic image display field 401 is displayed without being covered with the supplementary information display field 403. Therefore, even in a case in which the size of the display area of the display section 15 is relatively small, the user can perform diagnosis by viewing the entire ultrasonic image while checking the supplementary information.

The present disclosure can be applied to an image display apparatus that displays a medical image.

Although embodiments of the present invention have been described and illustrated in detail, the disclosed embodiments are made for purposes of illustration and example only and not limitation. The scope of the present invention should be interpreted by terms of the appended claims.

What is claimed is:

1. An image display apparatus, comprising:
  a display controller comprising a processor that performs display control on a display screen capable of receiving touch inputs included in a display section; and
  an operation acceptance section, wherein
  in a case where the operation acceptance section accepts a first operation of moving an operation position inward from a part of an edge portion of a display screen from a user in a state where a first display element is displayed on the display screen, the display controller displays a second display element having a first display size on the display screen, and resizes the second display element to a second display size in a case where a predetermined condition is satisfied;

wherein the first display element is a medical image used for diagnosis, and the second display element is a display field of at least one type from among a plurality of types of supplementary information that supplements the medical image, and based on a start position of the first operation at the edge portion of the display screen, the display controller determines a type of the supplementary information to be displayed in the second display element.

2. The image display apparatus according to claim 1, wherein the display controller displays the second display element based on the first operation such that the second display element is superimposed on at least a part of the first display element.

3. The image display apparatus according to claim 2, wherein the display controller causes the first display element to be displayed such that a region of interest of the first display element does not overlap the second display element.

4. The image display apparatus according to claim 1, wherein the display controller causes the second display element to be displayed such that at least a part of the first display element is visible through the second display element.

5. The image display apparatus according to claim 1, wherein based on the first operation, the display controller causes the second display element and the first display element to be displayed side by side on the display screen in a state where the first display element is reduced.

6. The image display apparatus according to claim 1, wherein the second display size is smaller than the first display size.

7. The image display apparatus according to claim 1, wherein when no new operation is accepted for a time equal to or longer than a predetermined time after the operation acceptance section accepts the first operation, the display controller determines that the predetermined condition is satisfied.

8. The image display apparatus according to claim 1, wherein when the operation acceptance section accepts a second operation of moving the second display element toward a part of the edge portion of the display screen, the display controller determines that the predetermined condition is satisfied.

9. The image display apparatus according to claim 1, wherein the display controller displays the second display element having the second display size at a position not overlapping the first display element.

10. The image display apparatus according to claim 1, wherein the supplementary information is at least any of a body mark, an annotation, measurement information indicating a measurement result in the medical image, patient information, or an image parameter.

11. The image display apparatus according to claim 10, further comprising:

an image generator that generates, based on an ultrasonic signal, an ultrasonic image to be displayed as the first display element, wherein the display controller makes different a type of the supplementary information to be displayed in the second display element based on the first operation, the type of the supplementary information being made different between a first display state in which the first display element is continuously updated and a second display state in which the ultrasonic image displayed as the first display element is not updated.

12. The image display apparatus according to claim 10, wherein the display controller makes different a type of the supplementary information to be displayed in the second display element based on the first operation, the type of the supplementary information being made different for each of a plurality of modes for generation of the ultrasonic image by the image generator.

13. An image display method of an image display apparatus including a display controller configured to perform display control on a display screen capable of receiving touch inputs included in a display section and an operation acceptance section, the image display method comprising:

causing a second display element having a second display size to be displayed on the display screen in a case where the operation acceptance section accepts a first operation of moving an operation position inward from a part of an edge portion of the display screen from a user in a state where a first display element having a first display size is displayed on the display screen; and resizing the second display element to a third display size when a predetermined condition is satisfied;

wherein the first display element is a medical image used for diagnosis, and the second display element is a display field of at least one type from among a plurality of types of supplementary information that supplements the medical image, and based on a start position of the first operation at the edge portion of the display screen, the display controller determines a type of the supplementary information to be displayed in the second display element.

14. A non-transitory computer-readable recording medium storing a program for a computer included in an image display apparatus including a display controller configured to perform display control on a display screen capable of receiving touch inputs included in a display section, and an operation acceptance section, the program causing the computer to perform processes of:

causing a second display element having a second display size to be displayed on the display screen in a case where the operation acceptance section accepts a first operation of moving an operation position inward from a part of an edge portion of the display screen from a user in a state where a first display element having a first display size is displayed on the display screen; and resizing the second display element to a third display size when a predetermined condition is satisfied;

wherein the first display element is a medical image used for diagnosis, and the second display element is a display field of at least one type from among a plurality of types of supplementary information that supplements the medical image, and based on a start position of the first operation at the edge portion of the display screen, the display controller determines a type of the supplementary information to be displayed in the second display element.

* * * * *